United States Patent
Zhang et al.

(10) Patent No.: US 10,746,833 B2
(45) Date of Patent: Aug. 18, 2020

(54) MAGNETIC RESONANCE VESSEL WALL IMAGING METHOD AND DEVICE

(71) Applicant: SHENZHEN INSTITUTES OF ADVANCED TECHNOLOGY CHINESE ACADEMY OF SCIENCES, Shenzhen, Guangdong (CN)

(72) Inventors: Lei Zhang, Guangdong (CN); Yiu-Cho Chung, Guangdong (CN); Xin Liu, Guangdong (CN); Xiaoqing Hu, Guangdong (CN); Hairong Zheng, Guangdong (CN)

(73) Assignee: SHENZHEN INSTITUTES ADVANCED TECHNOLOGY CHINESE ACADEMY OF SCIENCES, Shenzhen (CN)

(*) Notice: Subject to any disclaimer, the term of this patent is extended or adjusted under 35 U.S.C. 154(b) by 228 days.

(21) Appl. No.: 15/986,462

(22) Filed: May 22, 2018

(65) Prior Publication Data

US 2018/0267125 A1 Sep. 20, 2018

Related U.S. Application Data

(63) Continuation of application No. PCT/CN2016/104975, filed on Nov. 8, 2016.

(51) Int. Cl.
*G01R 33/565* (2006.01)
*G01R 33/56* (2006.01)
(Continued)

(52) U.S. Cl.
CPC ...... *G01R 33/56509* (2013.01); *A61B 5/0042* (2013.01); *A61B 5/02007* (2013.01);
(Continued)

(58) Field of Classification Search
CPC ........ G01R 33/56509; G01R 33/56508; G01R 33/5607; G01R 33/50; A61B 5/02007;
(Continued)

(56) References Cited

U.S. PATENT DOCUMENTS

| 5,614,826 A | 3/1997 | Dixon |
| 8,248,070 B1 | 8/2012 | Wheaton |

(Continued)

FOREIGN PATENT DOCUMENTS

| CN | 102692612 | 9/2012 |
| CN | 103930023 | 7/2014 |

OTHER PUBLICATIONS

Yibin Xie et al., "Improved Black-Blood Imaging Using DANTE-SPACE for Simultaneous Carotid and Intracranial Vessel Wall Evaluation", Magnetic Resonance in Medicine, Jul. 8, 2015, 9 pages.

(Continued)

*Primary Examiner* — Dixomara Vargas
(74) *Attorney, Agent, or Firm* — Bayramoglu Law Offices LLC

(57) ABSTRACT

A magnetic resonance vessel wall imaging method and device. The method comprises: applying a set pulse sequence into an imaging region, wherein the set pulse sequence comprises, in chronological order, a Delay Alternating with Nutation for Tailored Excitation (DANTE) pulse train, a variable flip angle train of a three-dimensional fast spin echo (SPACE), and a flip-down pulse train (S110); acquiring a magnetic resonance signal generated in the imaging region, and reconstructing a magnetic resonance images of the vessel wall in the imaging region according to the magnetic resonance signal (S120). By adding the flip-down pulse train behind the variable flip angle train of the three-dimensional fast spin echo (SPACE), the cerebrospinal (Continued)

—S130
Optimizing the variable flip angle train by adjusting longitudinal magnetization vector relaxation time T1 and/or transverse magnetization vector relaxation time T2, so as to improve a magnetic resonance image quality;

—S110
Applying a set pulse sequence into an imaging region, wherein the set pulse sequence comprises, in chronological order, a Delay Alternating with Nutation for Tailored Excitation (DANTE) pulse train, a variable flip angle train of a three-dimensional fast spin echo (SPACE), and a flip-down pulse train;

—S120
Acquiring a magnetic resonance signal generated in the imaging region, and reconstructing magnetic resonance images of the vessel wall in the imaging region according to the magnetic resonance signal.

fluid signals of the whole brain can be further suppressed effectively and uniformly, and the DANTE pulse train promotes the vessel wall imaging of the head and neck jointing portion.

30 Claims, 10 Drawing Sheets

(51) Int. Cl.

| | | |
|---|---|---|
| A61B 5/02 | (2006.01) | |
| G06T 11/00 | (2006.01) | |
| G01R 33/50 | (2006.01) | |
| A61B 5/055 | (2006.01) | |
| A61B 5/00 | (2006.01) | |
| G01R 33/563 | (2006.01) | |
| A61B 5/03 | (2006.01) | |

(52) U.S. Cl.
CPC ............ *A61B 5/055* (2013.01); *A61B 5/7207* (2013.01); *G01R 33/50* (2013.01); *G01R 33/5607* (2013.01); *G01R 33/5608* (2013.01); *G06T 11/00* (2013.01); *G06T 11/005* (2013.01); *A61B 5/032* (2013.01); *A61B 2576/026* (2013.01); *G01R 33/5635* (2013.01); *G06T 2210/41* (2013.01)

(58) Field of Classification Search
CPC ..... A61B 5/055; A61B 5/0042; A61B 5/7207; G06T 11/005; G06T 11/00
See application file for complete search history.

(56) References Cited

U.S. PATENT DOCUMENTS

| | | | | |
|---|---|---|---|---|
| 2013/0169274 A1* | 7/2013 | Yamashita | ............ | A61B 5/055 324/309 |
| 2013/0241554 A1* | 9/2013 | Yamashita | ............ | G01R 33/28 324/318 |
| 2013/0266200 A1* | 10/2013 | Miyazaki | ........... | G01R 33/5614 382/131 |
| 2013/0285655 A1* | 10/2013 | Miyazaki | ............. | G01R 33/543 324/309 |
| 2013/0314086 A1 | 11/2013 | Li et al. | | |
| 2013/0320978 A1* | 12/2013 | Nasiraei Moghaddam | ................ | G01R 33/543 324/309 |
| 2014/0194730 A1* | 7/2014 | Hoshino | .............. | A61B 5/0044 600/419 |
| 2015/0226821 A1* | 8/2015 | Zhang | ................ | G01R 33/4816 324/309 |
| 2015/0253402 A1* | 9/2015 | Yang | .................... | G01R 33/485 600/410 |
| 2015/0338489 A1* | 11/2015 | Nitta | .................. | A61B 5/14507 324/309 |
| 2016/0058319 A1* | 3/2016 | Shiodera | ................ | A61B 5/055 382/130 |
| 2016/0139222 A1* | 5/2016 | Frydman | .............. | G01R 33/483 324/309 |
| 2016/0266223 A1* | 9/2016 | Bi | ....................... | A61B 5/02007 |
| 2017/0315198 A1* | 11/2017 | Chen | .................... | G01R 33/448 |

OTHER PUBLICATIONS

First Chinese Office Action, issued in corresponding Chinese patent application No. 201680022139.3, dated Dec. 3, 2018, 6 pages.
Chinese Search Report, issued in corresponding Chinese patent application No. 201680022139.3, dated Dec. 3, 2018, 5 pages.
Chung et al., "High Resolution 3D Intracranial Imaging at 3.0T", Proc. Intl. Soc. Mag. Reson. Med., No. 18, p. 2255, 2010.
Mugler III et al., "Optimized Three-Dimensional Fast-Spin-Echo MRI", Journal of Magnetic Resonance Imaging, vol. 4, No. 39, p. 745-767, 2014.
Wang et al., "Joint blood and cerebrospinal fluid suppression for intracranial vessel wall MRI", Magnetic Resonance in Medicine, vol. 75, issue 2, 12 pages, Feb. 2016.
Li et al., DANTE-Prepared Pulse Trains: a Novel Approach to Motion-Sensitized and Motion-Suppressed Quantitative Magnetic Resonance Imaging, Magnetic Resonance in Medicine, vol. 5, No. 68, 16 pages, 2012.
Matsumae et al., "Velocity and Pressure Gradients of Cerebrospinal Fluid Assessed with Magnetic Resonance Imaging", J Neurosurg, vol. 120, pp. 218-227, Jan. 2014.
Park et al., "Optimized T1-Weighted Contrast for Single-Slab 3D Turbo Spin-Echo Imaging with Long Echo Trains: Application to Whole-Nrain Imaging", Magnetic Resonance in Medicine, vol. 58, pp. 982-992, 2007.
Viessmann et al., "T2-Weighted Intracranial Vessel Wall Imaging at 7 Tesla Using a DANTE-Prepared Variable Flip Angle Turbo Spin Echo Readout (DANTE-SPACE)", Magnetic Resonance in Medicine, vol. 77, pp. 655-663, 2017.

\* cited by examiner (a) (b) (c)

(a) (b) (c)

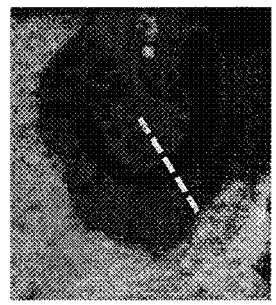 
Fig. 16A    Fig. 16B
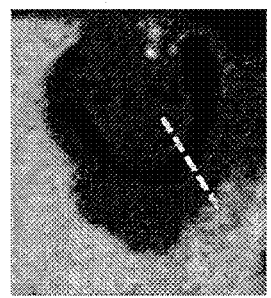 
Fig. 17A    Fig. 17B
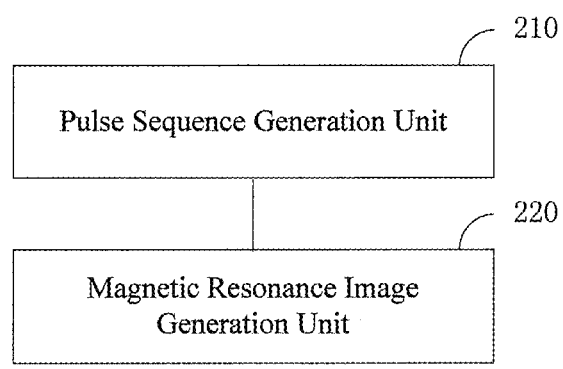
FIG. 18

MAGNETIC RESONANCE VESSEL WALL IMAGING METHOD AND DEVICE

CROSS-REFERENCE TO RELATED APPLICATIONS

This application is a continuation of International Application No. PCT/CN2016/104975, filed on Nov. 8, 2016, which are hereby incorporated by reference in their entireties.

TECHNICAL FIELD

The present invention relates to the field of magnetic resonance imaging techniques, and particularly, to a magnetic resonance vessel wall imaging method and device.

BACKGROUND

Stroke has been a disease of the highest mortality rate and disability rate in China. Among the 1.4 billion people in China, 16 million people die of stroke each year, and the mortality rate is 1.142%. The medical expenditure of stroke is huge, which brings heavy burdens to China. In 2004, the average hospitalization expense of Chinese stroke patients is RMB 6356, which is two times of the average annual income of urban and rural residents. Currently, the treatment expense of Chinese stroke patients is RMB 40 billion per year, which is ten times of the sum of the treatment expenses of other cardiovascular diseases. For this reason, early evaluation, early diagnosis and early prevention of stroke are particularly important.

Researches show that the main cause of stroke is that atherosclerosis vulnerable plaques rupture and the ruptured plaques form thrombose which cause a downstream vessel occlusion. In China, ischemic stroke is dominant, which occupies a proportion of about 80% of all strokes. Ischemic stroke is mainly caused by the lesions of intracranial artery (46.6%) and carotid artery (30%). Thus, the key of the early prevention and the precise treatment of stroke is to accurately recognize the structures and pathological characteristics of the intracranial and carotid artery plaques.

Magnetic Resonance (MR) vessel wall imaging is the currently unique means for noninvasively and panoramically displaying joint head and neck vessel walls and plaques. MR vessel wall imaging can noninvasively and accurately recognize the compositions and inflammatory activities in the plaques, and effectively evaluate the stability and vulnerability of the plaques, thus it is hopeful to bring new breakthrough to the early warning and diagnosis of stroke.

Dr. Chung Yiu-cho of Shenzhen Institutes of Advanced Technology cooperated with the Wasserman team of Johns Hopkins University, and proposed, for the first time, to realize the intracranial artery three-dimensional vessel wall imaging using the three-dimensional fast spin echo (SPACE) technique with T1 weighting (High Resolution 3D Intracranial Imaging at 3.0T, Proceedings of the 12th Annual Meeting of ISMRM, year 2010, page 2255), in the annual meeting of the International Society for Magnetic Resonance in Medicine (ISMRM). SPACE technique was developed from the fast spin echo (Optimized three-dimensional fast-spin-echo MRI, Journal of magnetic resonance imaging, year 2014, Issue 4, Volume 39, page 745), with high image acquisition efficiency, and could achieve black blood imaging without further preparing pulses. Dr. Chung Yiu-cho used T1 weighting to reduce the cerebrospinal fluid signals and make it easier to delinear the intracranial arterial vessel wall, meanwhile, they used the advanced 32-channel head radio frequency coil to increase the signal-to-noise ratio, thereby they successfully solved multiple key issues in the three-dimensional magnetic resonance intracranial artery imaging. SPACE technique was applied to the 3T Siemens imaging system to perform a T1 weighting three-dimensional magnetic resonance intracranial arterial wall imaging, thus 0.5 mm isotropous high-resolution three-dimensional black blood intracranial artery vessel wall image was obtained, with a scanning time of 10 minutes.

SPACE has intrinsic motion-sensitive characteristics, which could dephase the moving blood spins, and is widely used in the carotid artery vessel wall imaging. But the motion-sensitivity of SPACE is not that strong and a blood flow artifact will easily occur at the carotid bifurcation, thus other black blood module shall be added to more effectively suppress the blood flow signals. Recently, Mr. Wang J N combined SPACE technique with the Delay Alternating with Nutation for Tailored Excitation (DANTE) technique to suppress the cerebrospinal fluid signal and the blood flow signal at the same time, so as to increase contrast ratios between the vessel wall and the cerebrospinal fluid and the lumen (Joint blood and cerebrospinal fluid suppression for intracranial vessel wall MRI, Magnetic resonance in medicine, year 2015). As compared with the mere SPACE technique, the combination of SPACE and the DANTE can obtain better image of joint intracranial and extra cranial arterial wall. The DANTE is a new method for suppressing the signals of moving spins (DANTE-prepared pulse trains: a novel approach to motion-sensitized and motion-suppressed quantitative magnetic resonance imaging, Magnetic resonance in medicine, year 2012, Issue 5, Volume 68, page 1423), and its suppression effect on the carotid artery blood flow signal is obviously better than the other black blood techniques. Simulation shows that the DANTE can attenuate the spin signals for 80% with a moving velocity more than 0.2 cm/s, while the flow velocity of the cerebrospinal fluid is 0.1 to 2.0 cm/s, which just falls within the signal suppression range of the DANTE.

Although the DANTE can reduce the cerebrospinal fluid signals, its suppression on the cerebrospinal fluid signals is non-uniform. The DANTE causes the cerebrospinal fluid signals to be non-uniform in the reason that the DANTE is a motion-sensitive module, which can reduce more than 90% of the signal strength of a tissue with a moving velocity above 0.2 cm/s, while the signal strength of a tissue with a moving velocity below 0.2 cm/s is substantially unchanged. The cerebrospinal fluid is in a low motion state in the human brain, and its flow velocity varies in different regions within a range of 0.1 to 2 cm/s (Velocity and pressure gradients of cerebrospinal fluid assessed with magnetic resonance imaging, J Neurosurg, year 2014, Issue 1, Volume 120, page 218). Thus the DANTE achieves different degrees of signal suppression for the cerebrospinal fluid in different region of the brain, causing the cerebrospinal fluid signals non-uniform.

The non-uniform cerebrospinal fluid signals greatly affect the precise recognition of the intracranial vessel wall. Thus, how to uniformly and effectively suppress the cerebrospinal fluid signals becomes a key issue for further improving the vessel wall imaging quality.

SUMMARY

The present invention provides a magnetic resonance vessel wall imaging method and device, so as to uniformly and effectively suppress the cerebrospinal fluid signals of head and neck jointing portion, and improve the vessel wall imaging quality.

The present invention provides a magnetic resonance vessel wall imaging method, comprising: applying a set pulse sequence into an imaging region, wherein the set pulse sequence comprises, in chronological order, a Delay Alternating with Nutation for Tailored Excitation (DANTE) pulse train, a variable flip angle train of a three-dimensional fast spin echo (SPACE), and a flip-down pulse train; and acquiring a magnetic resonance signal generated in the imaging region, and reconstructing magnetic resonance images of the vessel wall in the imaging region according to the magnetic resonance signal.

The present invention further provides a magnetic resonance vessel wall imaging device, comprising: a pulse generation unit configured to apply a set pulse sequence into an imaging region, wherein the set pulse sequence comprises, in chronological order, a Delay Alternating with Nutation for Tailored Excitation (DANTE) pulse train, a variable flip angle train of a three-dimensional fast spin echo (SPACE), and a flip-down pulse train; and a magnetic resonance image generation unit configured to acquire a magnetic resonance signal generated in the imaging region, and reconstruct magnetic resonance images of the vessel wall in the imaging region according to the magnetic resonance signal.

The present invention further provides a computer readable storage medium comprising computer readable instructions, wherein the computer readable instructions enable, when being executed, a processor to at least perform the above method.

The present invention further provides an equipment, comprising: a memory comprising computer readable instructions; and a processor configured to, when the computer readable instructions are executed, perform the above method.

By creatively designing a pulse sequence, and adding a flip-down pulse train behind the variable flip angle train of the three-dimensional fast spin echo (SPACE), the magnetic resonance vessel wall imaging method and device and the computer readable storage medium provided by the present invention effectively and uniformly further suppress the cerebrospinal fluid signals of the whole brain, remedy the defect that the DANTE technique cannot uniformly suppress the cerebrospinal fluid signals, and further improve the magnetic resonance vessel wall imaging quality based on the technique combining the existed DANTE and SPACE. By adding a Delay Alternating with Nutation for Tailored Excitation (DANTE) pulse train in front of the variable flip angle train of the three-dimensional fast spin echo (SPACE), the advantages of DANTE can be remained to effectively suppress the blood flow signals, which promotes the vessel wall imaging of the head and neck jointing portion. In other embodiments, by optimizing the variable flip angle train of SPACE, the signal-to-noise ratio of the magnetic resonance image can be further improved.

BRIEF DESCRIPTION OF DRAWINGS

In order to more clearly describe the technical solutions in the embodiments of the present invention or the prior art, the drawings used in the description of the embodiments or the prior art will be briefly introduced as follows. Obviously, the drawings in the following description just illustrate some embodiments of the present invention, and a person skilled in the art can obtain other drawings from them without paying any creative effort. In which.

FIGS. 16A and 16B respectively illustrate a long axis magnetic resonance image and a short-axis magnetic resonance image of a vessel wall obtained using the variable flip angles when T1/T2 is 940/100 ms as illustrated in FIG. 14;

FIGS. 17A and 17B respectively illustrate a long axis magnetic resonance image and a short-axis magnetic resonance image of a vessel wall obtained using the variable flip angles when T1/T2 is 1000/150 ms as illustrated in FIG. 14;

FIG. 18 illustrates a structure diagram of a magnetic resonance vessel wall imaging device in an embodiment of the present invention;

DESCRIPTION OF EMBODIMENTS

In order to make the objective, the technical solutions and the advantages of the embodiments of the present invention clearer, the embodiments of the present invention will be further described in details as follows with reference to the drawings. The illustrative embodiments and description thereof herein are just used to explain the present invention, rather than limitations to the present invention.

Based on the problem encountered by the existed SPACE-DANTE combination technique when performing a vessel wall magnetic resonance imaging, the present invention redesigns the pulse sequence for magnetic resonance imaging, and on this basis, proposes a magnetic resonance vessel wall imaging method, which more effectively and uniformly suppresses the cerebrospinal fluid signals while increasing the signal-to-noise ratio of the tissue, as compared with the existed SPACE-DANTE combination technique. To be noted in advance, the following embodiments just describe the implementations and effects of the present invention through the examples of intracranial vessel wall magnetic resonance imaging, carotid artery vessel wall magnetic resonance imaging, and suppression of cerebrospinal fluid signals, rather than limiting the imaging regions and purposes of the present invention. A person skilled in the art acquires that the methods of the embodiments of the present invention can also be used for imaging the vessel walls of other parts of a human or animal body, and suppressing other body fluid signals having imaging characteristics similar to those of the cerebrospinal fluid and the carotid artery blood flow. Thus, the protection scope of the present invention shall be determined by the claims.

Figure 1:
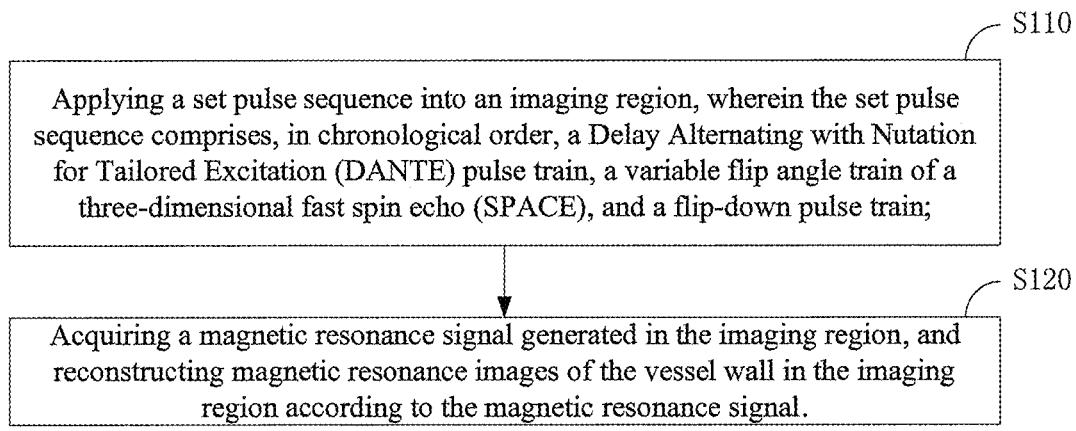
FIG. 1 illustrates a flow diagram of a magnetic resonance vessel wall imaging method in an embodiment of the present invention.

FIG. 1 illustrates a flow diagram of a magnetic resonance vessel wall imaging method in an embodiment of the present invention. As illustrated in FIG. 1, a magnetic resonance vessel wall imaging method in an embodiment of the present invention comprises the steps of:

S110: applying a set pulse sequence into an imaging region, wherein the set pulse sequence comprises, in chronological order, a Delay Alternating with Nutation for Tailored Excitation (DANTE) pulse train, a variable flip angle train of a three-dimensional fast spin echo (SPACE), and a flip-down pulse train;

S120: acquiring a magnetic resonance signal generated in the imaging region, and reconstructing magnetic resonance images of the vessel wall in the imaging region according to the magnetic resonance signal.

In step S110, the DANTE pulse train may be an existed one, such as a DANTE pulse train used by Li L Q, etc. (DANTE-prepared pulse trains: a novel approach to motion-sensitized and motion-suppressed quantitative magnetic resonance imaging, Magnetic resonance in medicine, Issue 5, Volume 68, page 1423, year 2012). The variable flip angle train of SPACE may be an existed one, such as a variable flip angle train of SPACE initially proposed by Dr. Chung Yiu-cho of Shenzhen Institutes of Advanced Technology and the Wasserman team of Johns Hopkins University in the annual meeting of International Society for Magnetic Resonance in Medicine (ISMRM), or a variable flip angle train of SPACE improved based on the existed variable flip angle train of SPACE.

In some embodiments, in step S110, the DANTE pulse train may comprise a plurality of pulse modules arranged in chronological order, each comprising one rectangular pulse and one dephasing gradient. The rectangular pulse is a pulse of several or a dozen of degrees, and for example 2° to 20°, such as 10°. The amplitude of the dephasing gradient may be set as a maximum value of the magnetic resonance system, such as 20 mT/m to 40 mT/m. The time duration of one pulse module may be about 1.5 ms, such as 1 ms to 2 ms. The number of repetitions of the pulse module may be adjusted depending on the application conditions, and for example may be in the range of 50 to 500. The DANTE pulse train can effectively suppress the blood flow artifacts at the carotid artery and the intracranial artery, and increase the contrast ratio between the lumen and the vessel wall.

The flip-down pulse train may be an existed one, such as a flip-down pulse train used by Park, etc. in "Optimized T1-weighted contrast for single-slab 3D turbo spin-echo imaging with long echo trains: application to whole-brain imaging" (Magn Reson Med, year 2007, Issue 5, Volume 58, page 982).

In some embodiments, in step S110, the flip-down pulse train may comprise, in chronological order, the first pulse, the second pulse and the third pulse; wherein a time interval between the first pulse and the second pulse may be one echo spacing, a time interval between the second pulse and the third pulse may be a half of one echo spacing, and the flip angle of the third pulse is 90°. The echo spacing preferably takes a value as small as possible, such as a minimum echo spacing allowed by the magnetic resonance system.

In some embodiments, the first pulse is 130°, and the second pulse is 160°. In other embodiments, the first pulse may be around 130°, and the second pulse may be around 160°. For example, the flip angle of the first pulse is in the range of 100° to 150°, and the second pulse is in the range of 140° to 180°.

To be noted, although the flip-down pulse train in the embodiments of the present disclosure may be the same as that in "Optimized T1-weighted contrast for single-slab 3D turbo spin-echo imaging with long echo trains: application to whole-brain imaging" (Magn Reson Med, year 2007, Issue 5, Volume 58, page 982), their functions are different from each other. The former is to suppress the cerebrospinal fluid signals, and the latter is to increase the contrast ratio between the grey and white matters.

In some embodiments, the set pulse sequence may only comprise a DANTE pulse train, a variable flip angle train of SPACE and the flip-down pulse train, wherein the DANTE pulse train may be adjacent to the variable flip angle train of SPACE, and the variable flip angle train of SPACE generally may be adjacent to the flip-down pulse train. In some other embodiments, the set pulse sequence may further comprise other pulse at the same time, and its position relative to the DANTE pulse train, the variable flip angle train of SPACE and the flip-down pulse train in chronological order may be set upon demand.

The pulse used for magnetic resonance imaging is designed by enabling the set pulse sequence to comprise, in chronological order, a Delay Alternating with Nutation for Tailored Excitation (DANTE) pulse train, a variable flip angle train of a three-dimensional fast spin echo (SPACE), and a flip-down pulse train. By being disposed in the set pulse sequence, the DANTE pulse train retains the advantage of suppressing the blood flow signals of head and neck jointing portion. By disposing the variable flip angle train of SPACE in the set pulse sequence, SPACE retains the advantages of high image acquisition efficiency, good contrast ratio between the vessel wall and the cerebrospinal fluid, and no preparation pulse is required to achieve a black blood effect. By adding the flip-down pulse train behind the variable flip angle train of SPACE, the cerebrospinal fluid signals can be further suppressed uniformly, so as to remedy the defect that the DANTE pulse train cannot uniformly suppress the cerebrospinal fluid signals, and improve the contrast ratio between the cerebrospinal fluid and the vessel wall, and differentiability of the vessel wall. In this way, it not only improves the intracranial vessel wall imaging quality, but also promotes vessel wall imaging of the head and neck jointing portion.

In step S120, after the set pulse sequence is applied into the imaging region, magnetic resonance signals are successively excited by the variable flip angle train of SPACE and the flip-down pulse train. The magnetic resonance signals may be acquired with an existed or improved acquisition method. For example, the magnetic resonance signals may be obtained through the processes such as pulse, slab selective gradient, read-out gradient and phase encoding. The vessel wall magnetic resonance image in the imaging region may be obtained from the acquired magnetic resonance signals through for example a magnetic resonance image reconstruction algorithm. The above step can be achieved by a person skilled in the art according to the set pulse sequence in the embodiment of the present invention or the prior art, which is omitted herein.

The magnetic resonance vessel wall imaging method in the embodiment of the present invention particularly makes a pulse sequence to comprise a DANTE pulse train, a variable flip angle train of SPACE and a flip-down pulse train, so as to further uniformly suppress the cerebrospinal fluid signals based on the technology that combines the existed SPACE and DANTE, which not only improves the intracranial vessel wall imaging quality, but also promotes the vessel wall imaging of the head and neck jointing portion.

Figure 2:
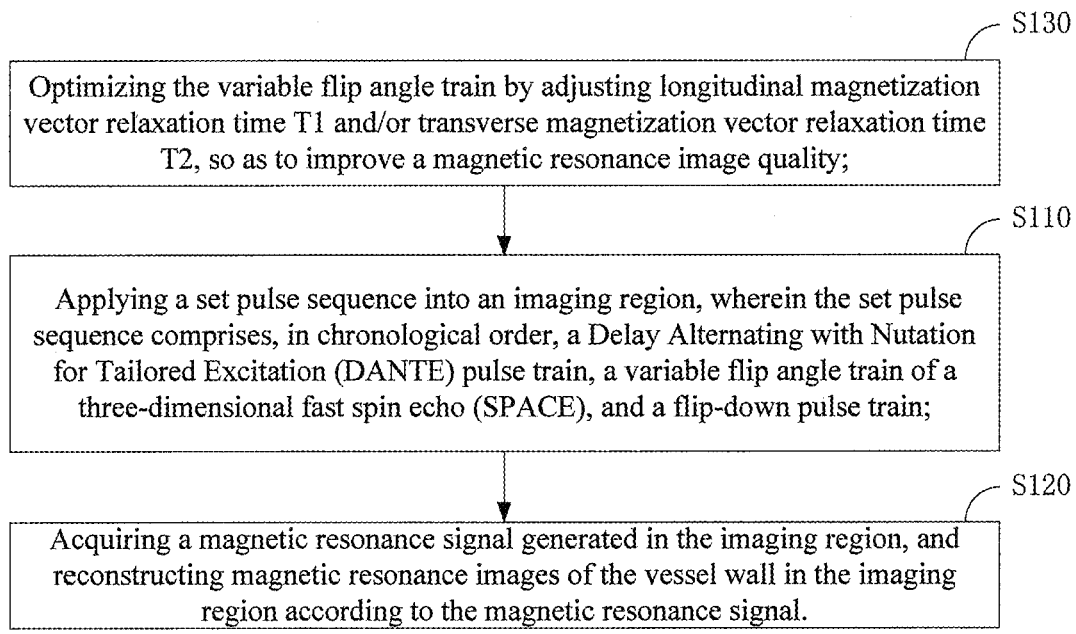
FIG. 2 illustrates a flow diagram of a magnetic resonance vessel wall imaging method in another embodiment of the present invention.

FIG. 2 illustrates a flow diagram of a magnetic resonance vessel wall imaging method in another embodiment of the present invention. As illustrated in FIG. 2, before step S110, i.e., applying a set pulse sequence into an imaging region, the magnetic resonance vessel wall imaging method as illustrated in FIG. 1 may further comprise:

S130: optimizing the variable flip angle train by adjusting longitudinal magnetization vector relaxation time T1 and/or transverse magnetization vector relaxation time T2, so as to improve a magnetic resonance image quality.

In step S130, the variable flip angle train of SPACE may be optimized by adjusting one or both of the longitudinal magnetization vector relaxation time T1 and the transverse magnetization vector relaxation time T2. In a preferred embodiment, the longitudinal magnetization vector relaxation time T1 and/or the transverse magnetization vector relaxation time T2 may be adjusted into different values for magnetic resonance systems of different magnetic field strength. In one embodiment, regarding a 3T magnetic resonance system, the transverse magnetization vector relaxation time T2 may be adjusted into a range of 150 ms to 200 ms, and for example the value of T2 may be set as 150 ms, 165 ms or 175 ms; meanwhile or optionally, the longitudinal magnetization vector relaxation time T1 may be adjusted into a range of 800 ms to 3000 ms, and for example the value of T1 may be set as 1000 ms, 1500 ms or 2000 ms.

Figure 3:
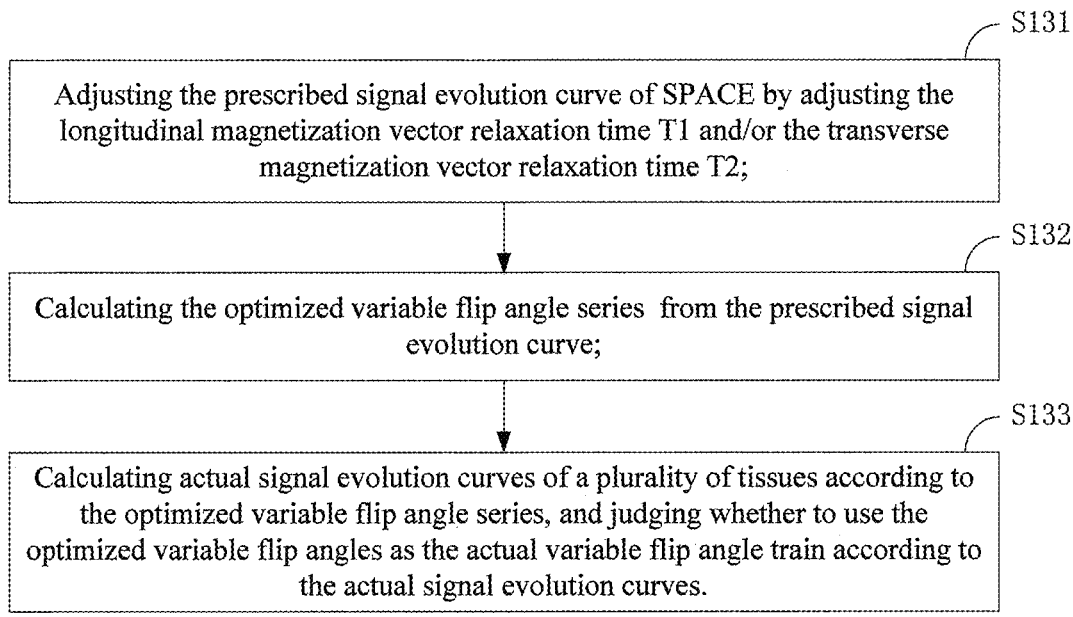
FIG. 3 illustrates a flow diagram of a method for optimizing a variable flip angle train of SPACE in an embodiment of the present invention.

FIG. 3 illustrates a flow diagram of a method for optimizing a variable flip angle train of SPACE in an embodiment of the present invention. As illustrated in FIG. 3, in step S130, the method for optimizing the variable flip angle train by adjusting longitudinal magnetization vector relaxation time T1 and/or transverse magnetization vector relaxation time T2 may comprise the steps of:

S131: adjusting the prescribed signal evolution curve of SPACE by adjusting the longitudinal magnetization vector relaxation time T1 and/or the transverse magnetization vector relaxation time T2;

S132: calculating the optimized variable flip angle series from the prescribed signal evolution curve;

S133: calculating actual signal evolution curves of a plurality of tissues according to the optimized variable flip angle series, and judging whether to use the optimized variable flip angles as the actual variable flip angle train according to the actual signal evolution curves.

In step S131, the prescribed signal evolution curve of SPACE may be adjusted by adjusting one or both of the longitudinal magnetization vector relaxation time T1 and the transverse magnetization vector relaxation time T2. Preferably, the prescribed signal evolution curve of SPACE may be adjusted by adjusting the longitudinal magnetization vector relaxation time T1 and/or the transverse magnetization vector relaxation time T2 for different magnetic resonance magnetic fields. In one embodiment, the prescribed signal evolution curve of SPACE may be only adjusted for one type of set imaging tissue.

In some embodiments, the magnetic resonance vessel wall imaging method is based on the 3T magnetic resonance system. In step S131, the method for adjusting the prescribed signal evolution curve of SPACE by adjusting the longitudinal magnetization vector relaxation time T1 and/or the transverse magnetization vector relaxation time T2, may be implemented by setting the prescribed signal evolution curve of SPACE by setting the longitudinal magnetization vector relaxation time T1 in the range of 800 ms to 3000 ms, and/or setting the transverse magnetization vector relaxation time T2 in the range of 150 ms to 200 ms.

In some embodiments, in the above steps, the method for setting the prescribed signal evolution curve of SPACE by setting the longitudinal magnetization vector relaxation time T1 as 800 ms to 3000 ms; and/or setting the transverse magnetization vector relaxation time T2 as 150 ms to 200 ms may be implemented by setting the prescribed signal evolution curve of SPACE by setting the longitudinal magnetization vector relaxation time T1 as 1000 ms, and/or setting the transverse magnetization vector relaxation time T2 as 150 ms.

In step S133, the plurality of tissues may be a number of different tissues in the imaging region or other regions, such as cerebrospinal fluid, grey matter, white matter, etc. After the actual signal evolution curves of the plurality of tissues are obtained, the signal difference between two target tissues may be determined whether to take the optimized variable flip angles as the actual variable flip angle train of SPACE.

In one embodiment, if the actual signal evolution curve of different tissues do not meet the set requirement (e.g., the actual contrast between different tissues do not meet the set range), step S131 may be repeated to re-adjust the longitudinal magnetization vector relaxation time T1 and/or the transverse magnetization vector relaxation time T2, recalculate the variable flip angles using step S132, and recalculate the actual signals of different tissues according to the recalculated variable flip angles using step S133 until they meet the set requirement.

In the present embodiment, the variable flip angle train of the existed SPACE is optimized through steps S131 to S133, and the variable flip angle train of the optimized SPACE is used for the set pulse sequence, so as to further increase the contrast ratio between the vessel wall and the cerebrospinal fluid, thereby improving the imaging effect of existed SPACE.

Figure 4:
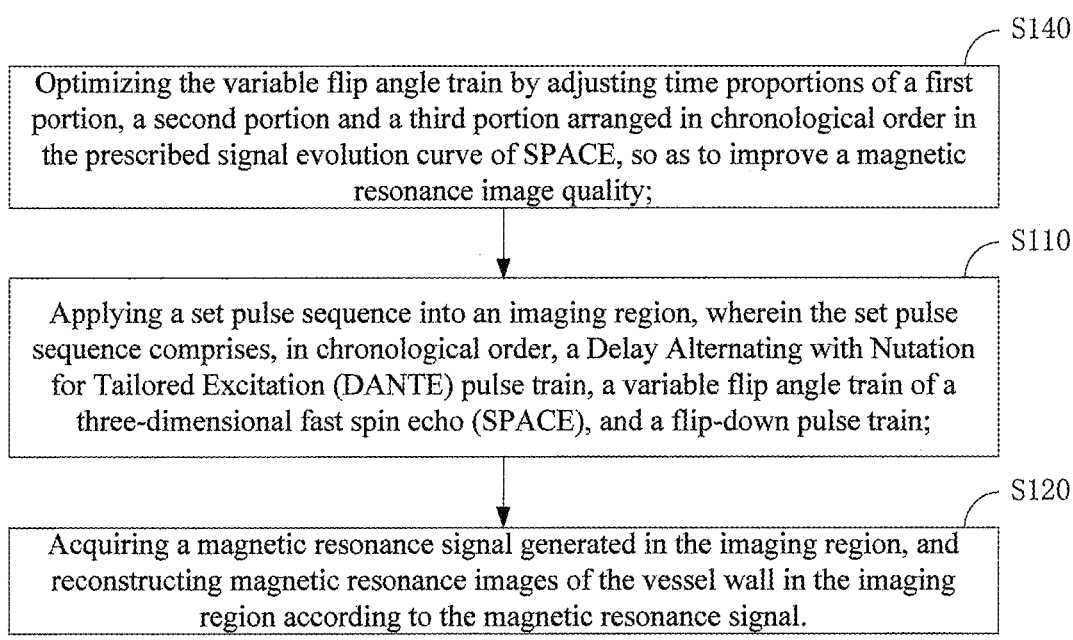
FIG. 4 illustrates a flow diagram of a magnetic resonance vessel wall imaging method in still another embodiment of the present invention.

FIG. 4 illustrates a flow diagram of a magnetic resonance vessel wall imaging method in another embodiment of the present invention. As illustrated in FIG. 4, before step S110, i.e., applying a set pulse sequence into an imaging region, the magnetic resonance vessel wall imaging method as illustrated in FIG. 1 may further comprise:

S140: optimizing the variable flip angle train by adjusting time proportions of a first portion, a second portion and a third portion arranged in chronological order in the prescribed signal evolution curve of SPACE, so as to improve a magnetic resonance image quality.

Generally, the prescribed signal evolution curve of SPACE may comprise three portions, i.e., the first portion, the second portion and the third portion. Usually, the first portion is an initial attenuation portion and the signal decreases exponentially during this portion; the second portion has a signal strength remaining unchanged, and it is an intermediate flat portion; and the third portion has a signal strength continuously decreased along with the time, and it is a final attenuation portion.

In some embodiments, the length of the first portion may be in the range of 2 to 5 echoes of the SPACE, duration of the second portion may be in the range of 40% to 70% of total duration of the prescribed signal evolution curve, and the rest time may be the time occupied by the third portion.

The various portions in the prescribed signal evolution of SPACE have different functions. The initial exponential decay portion may be used for driving the transverse magnetization vector to reach a steady state; the echo signal of the intermediate flat portion may fill the K-space center, which is the most important portion of the echo train, this portion can directly determine the signal-to-noise ratio and the contrast ratio of the image and the point spread function of a single pixel; the signal of the final attenuation portion is mainly used to adjust the strength of the intermediate signal, the whole signal strength increases when the final portion decreases more rapidly.

In the present embodiment, the prescribed signal evolution of the optimized SPACE can be obtained by reasonably adjusting the time proportions of various portions in the prescribed signal evolution curve of SPACE, e.g., adjusting the length of the first portion to be 2 to 5 echoes of the SPACE, and adjusting the duration of the second portion to be 40% to 70% of the total duration of the prescribed signal evolution curve, so as to optimize the variable flip angle train of SPACE and improve the magnetic resonance image quality.

Figure 5:
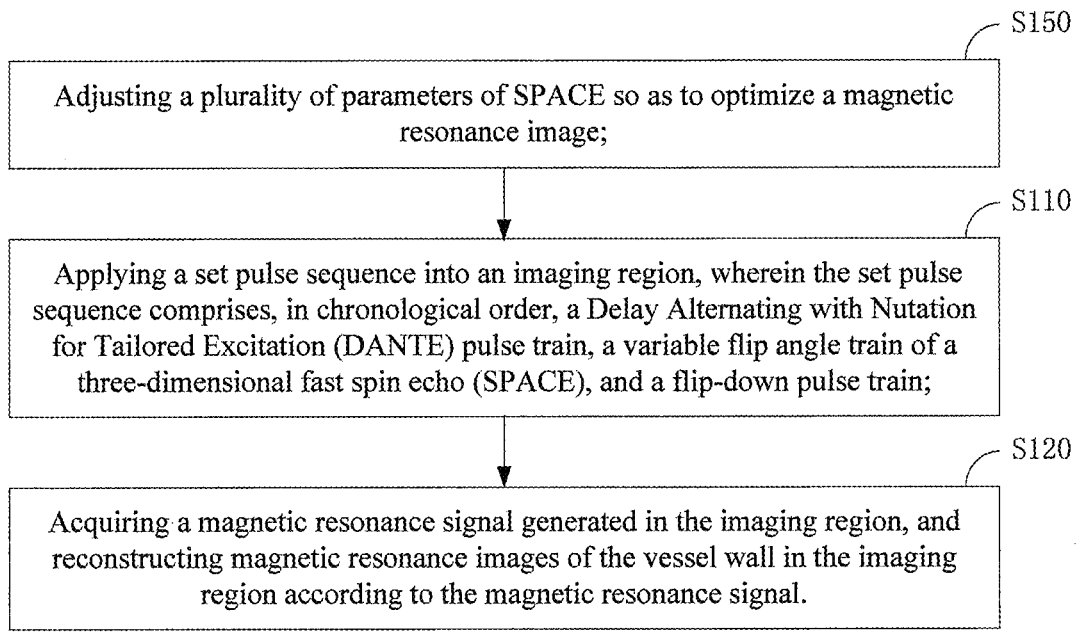
FIG. 5 illustrates a flow diagram of a magnetic resonance vessel wall imaging method in yet another embodiment of the present invention.

FIG. 5 illustrates a flow diagram of a magnetic resonance vessel wall imaging method in yet another embodiment of the present invention. As illustrated in FIG. 5, before step S110, i.e., applying a set pulse sequence into an imaging region, the magnetic resonance vessel wall imaging method as illustrated in FIG. 1 may further comprise:

S150: adjusting a plurality of parameters of SPACE so as to optimize a magnetic resonance image.

In which, the repetition time TR of SPACE is in the range of 800 ms to 1200 ms, echo TE of SPACE is in the range of 5 ms to 25 ms, and an echo train length of SPACE is in the range of 25 to 60.

In the present embodiment, SPACE effect can be optimized by adjusting the repetition time TR, the echo time TE and the echo train length of SPACE into their reasonable ranges, respectively, thereby further improving the magnetic resonance image quality of the imaging region.

Figure 6:
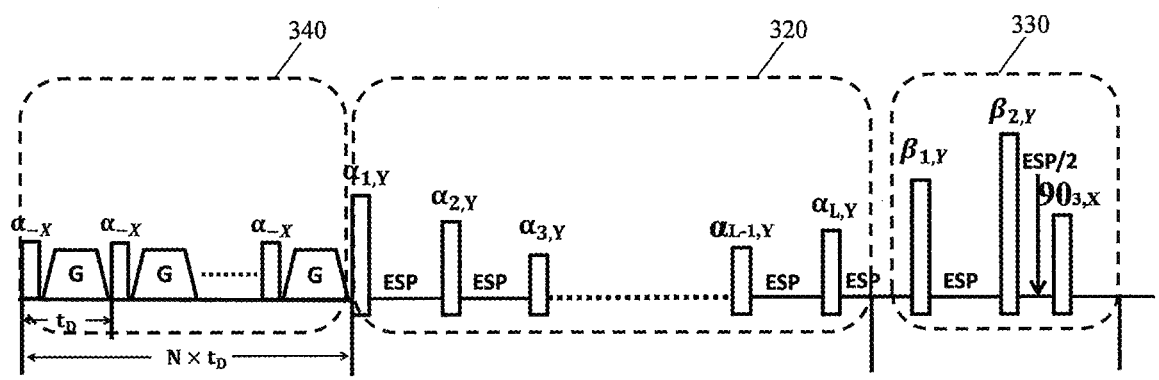
FIG. 6 illustrates a schematic diagram of a set pulse sequence in an embodiment of the present invention.

FIG. 6 illustrates a schematic diagram of a set pulse sequence in an embodiment of the present invention. As illustrated in FIG. 6, the set pulse sequence comprises a DANTE pulse train 340, a variable flip angle train of SPACE 320 and a flip-down pulse train 330. The DANTE pulse train 340 may comprise a plurality of pulse modules, each comprising a pulse $\alpha_{-X}$ and a dephasing gradient G. The pulse $\alpha_{-X}$ may be a none selective pulse, $\alpha_{-X} \approx 10°$. The amplitude of the dephasing gradient G may be set as a maximum value of the magnetic resonance system, such as 20 mT/m to 40 mT/m. The time duration $t_D$ of one pulse module may be about 1.5 ms, such as 1 ms to 2 ms. The number N of repetitions of the pulse module may be adjusted depending on the application conditions, and for example may be set as 50 to 500. The DANTE pulse train 340 may be designed with reference to that recorded in "T2-Weighted Intracranial Vessel Wall Imaging at 7 Tesla Using a DANTE-Prepared Variable Flip Angle Turbo Spin Echo Readout (DANTE-SPACE)" (Magnetic Resonance in Medicine, year 2016), "Joint blood and cerebrospinal fluid suppression for intracranial vessel wall MRI" (Magnetic resonance in medicine, year 2015), or "DANTE-prepared pulse trains: a novel approach to motion-sensitized and motion-suppressed quantitative magnetic resonance imaging" (Magnetic resonance in medicine, Issue 5, Volume 68, page 1423, year 2012). The variable flip angle train of SPACE 320 may comprise pulse $\alpha_{1,Y}$, pulse $\alpha_{2,Y}$, pulse $\alpha_{3,Y}$, ..., pulse $\alpha_{L-1,Y}$ and pulse $\alpha_{L,Y}$, wherein L is an integer larger than or equal to 1, and an interval between those pulses is one echo spacing ESP. The flip-down pulse train 330 may comprise pulse $\beta_{1,Y}$, pulse $\beta_{2,Y}$ and 90° pulse $90_{3,X}$, wherein an interval between pulse $\beta_{1,Y}$ and pulse $\beta_{2,Y}$ is one echo spacing ESP, and an interval between pulse $\beta_{2,Y}$ and 90° pulse $90_{3,X}$ is a half of one echo spacing ESP/2.

Figure 7:
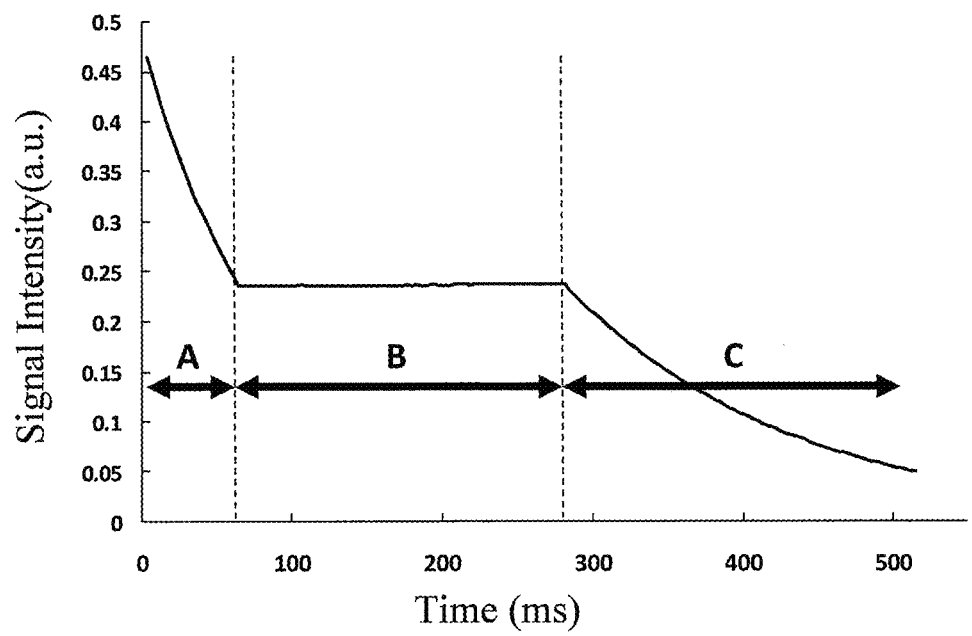
FIG. 7 illustrates a curve diagram of a prescribed signal evolution of SPACE in an embodiment of the present invention.
Figure 8:
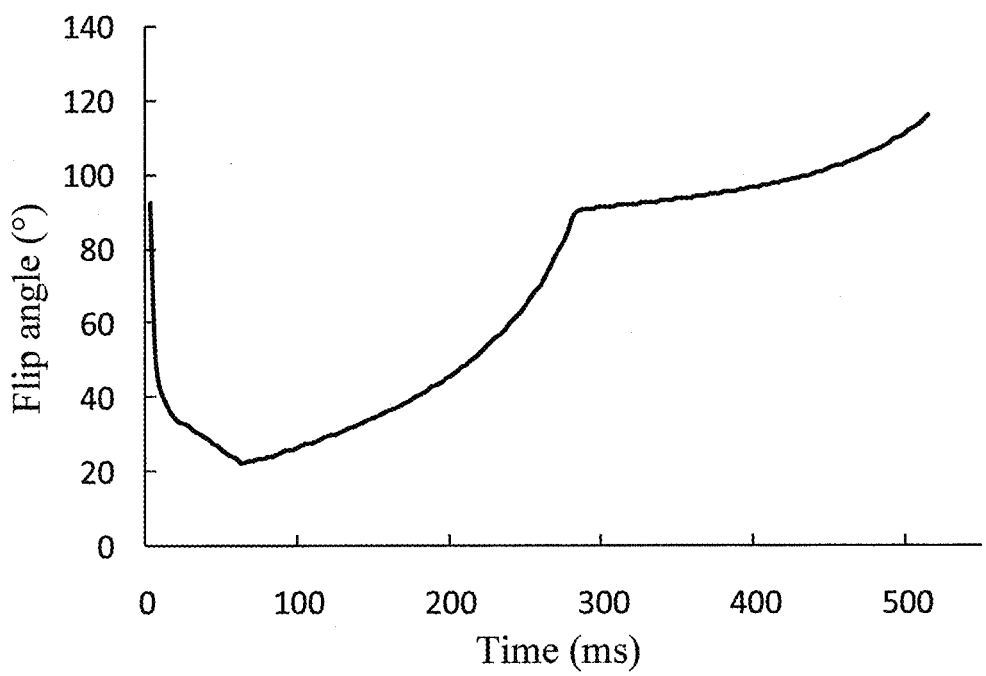
FIG. 8 illustrates a variable flip angle train calculated from the prescribed signal evolution of SPACE as illustrated in FIG. 7.
Figure 9:
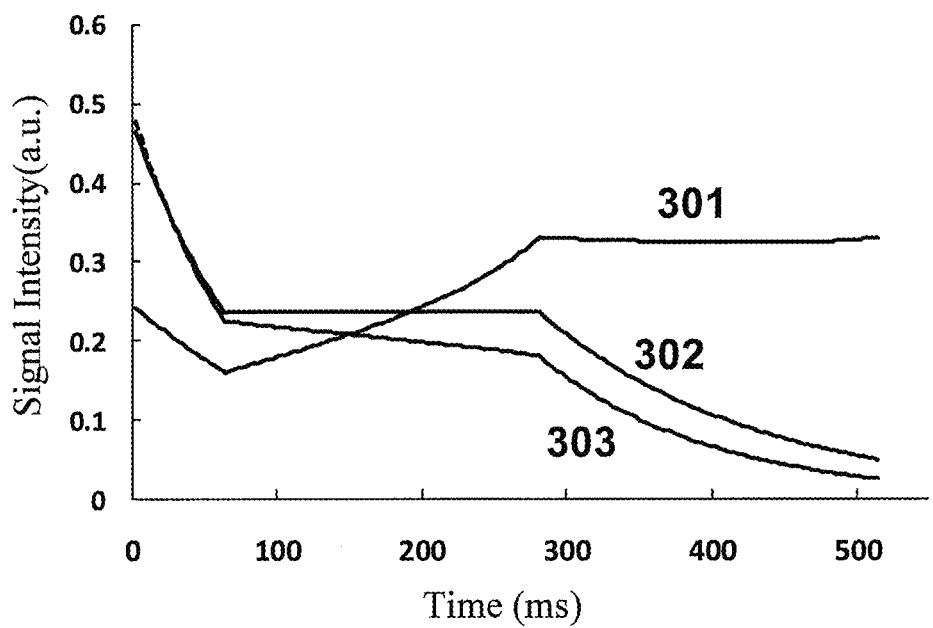
FIG. 9 illustrates an actual signal evolution curves of different tissues calculated from the variable flip angle train as illustrated in FIG. 8.

FIG. 7 illustrates a curve diagram of a prescribed signal evolution of SPACE in an embodiment of the present invention. As illustrated in FIG. 7, a prescribed signal evolution curve of SPACE is designed for a particular tissue, comprising an initial attenuation portion A, an intermediate flat portion B and a final attenuation portion C. Wherein the initial attenuation portion A may have a length of 3 echoes, the duration of the intermediate flat portion B may be 65%, and the rest time is the final attenuation portion. Based on the 3T magnetic resonance system, the longitudinal magnetization vector relaxation time T1 and the transverse magnetization vector relaxation time T2 may be 1000 ms and 150 ms, respectively. FIG. 8 illustrates a variable flip angle train calculated from the prescribed signal evolution of SPACE as illustrated in FIG. 7. FIG. 9 illustrates an actual signal evolution curves of different tissues calculated from the variable flip angle train as illustrated in FIG. 8. As illustrated in FIG. 9, the prescribed signal evolution of SPACE designed in the present embodiment can well distinguish cerebrospinal fluid 301, grey matter 302 and white matter 303 from each other, which proves that the prescribed signal evolution of SPACE designed in the present embodiment optimizes the variable flip angle train of SPACE.

Figure 10:
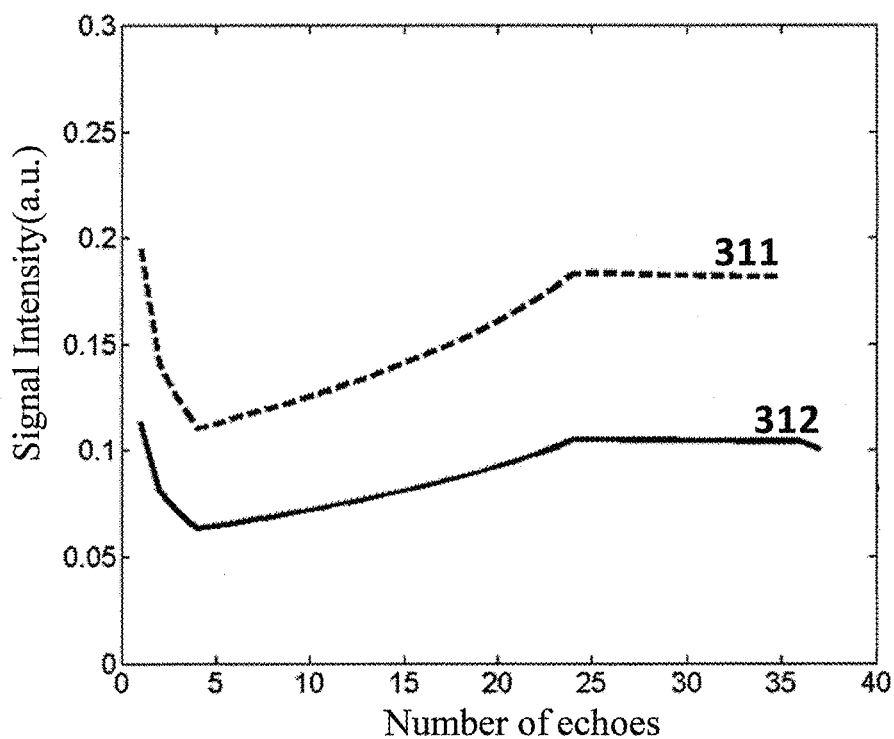
FIG. 10 illustrates a schematic diagram of a simulation result comparing the cerebrospinal fluid signal using a method of an embodiment of the present invention and existed SPACE, respectively.

FIG. 10 illustrates a schematic diagram of a simulation result comparing the cerebrospinal fluid signal using a method of an embodiment of the present invention and existed SPACE, respectively. As illustrated in FIG. 10, relative to a cerebrospinal fluid signal 311 generated by the existed SPACE, a cerebrospinal fluid signal 312 generated by combining SPACE and the flip-down pulse train in the embodiment of the present invention has its strength obviously decreased. It is clear that by adding the flip-down pulse train behind the variable flip angle train of SPACE, the method of the embodiment of the present invention can indeed suppress the cerebrospinal fluid signal.

Figure 11:
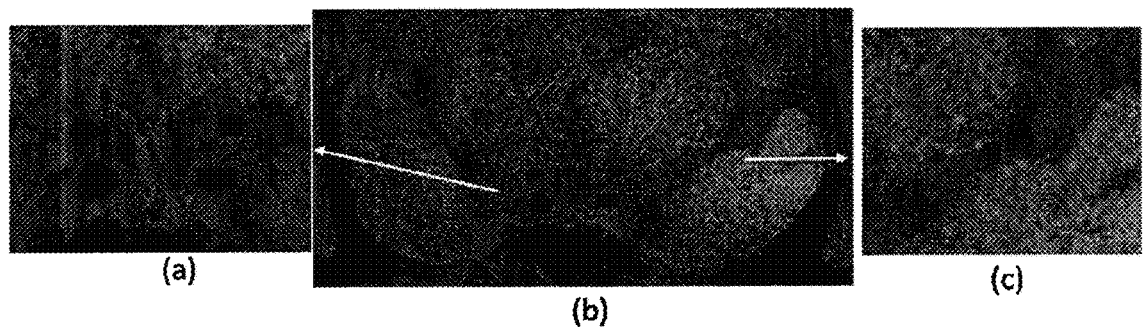
FIGS. 11 and 12 respectively illustrate magnetic resonance images of a same imaging region obtained using existed SPACE-DANTE and a method of an embodiment of the present invention.
Figure 12:
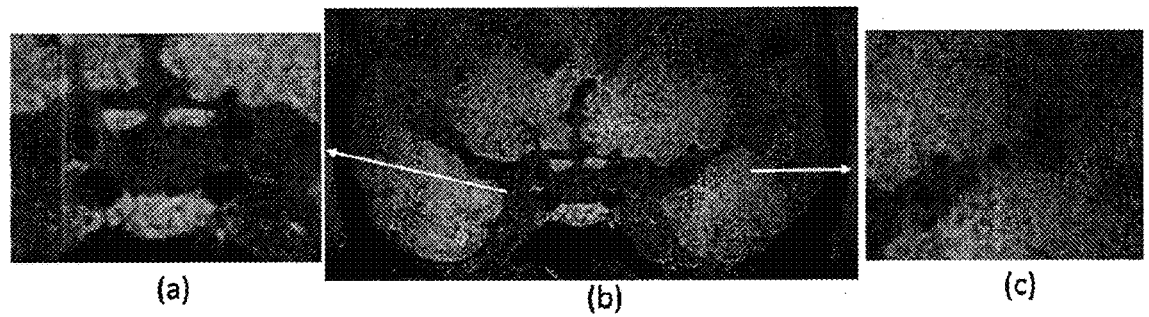

FIGS. 11 and 12 respectively illustrate magnetic resonance images of a same imaging region obtained using existed SPACE-DANTE and a method of an embodiment of the present invention. The magnetic resonance image as illustrated in FIG. 11 is obtained according to the DANTE-SPACE method proposed by Wang J N, etc. (Joint blood and cerebrospinal fluid suppression for intracranial vessel wall MRI, Magnetic resonance in medicine, year 2015). As illustrated in FIG. 11, parts (a) and (c) are enlarged images of corresponding positions in part (c). As illustrated in FIG. 12, parts (a) and (c) are enlarged images of corresponding positions in part (c). Part (a) of FIG. 11 and part (a) of FIG. 12 illustrate the situations of suppressing the cerebrospinal fluid near the circle of Wills. By comparing the gray levels of part (a) of FIG. 11 and part (a) of FIG. 12, it can be seen that the method of the embodiment of the present invention combines the DANTE pulse train, SPACE and the flip-down pulse train so as to more uniformly and efficiently suppress the cerebrospinal fluid signal near the circle of Willis. Part (c) of FIG. 11 and part (c) of FIG. 12 illustrate the situations of suppressing the cerebrospinal fluid in M2 segment of middle cerebral artery. By comparing the gray levels of part (c) of FIG. 11 and part (c) of FIG. 12, it can be seen that the method of the embodiment of the present invention can more uniformly and efficiently suppress the cerebrospinal fluid signal of M2 segment of middle cerebral artery, and more clearly display the outer boundary of the intracranial vessel wall. Thus, as compared with the prior art, the method of the embodiment of the present invention can more uniformly suppress the cerebrospinal fluid signal of the whole brain, and clearly display the outer boundary of the intracranial vessel wall.

Figure 13:
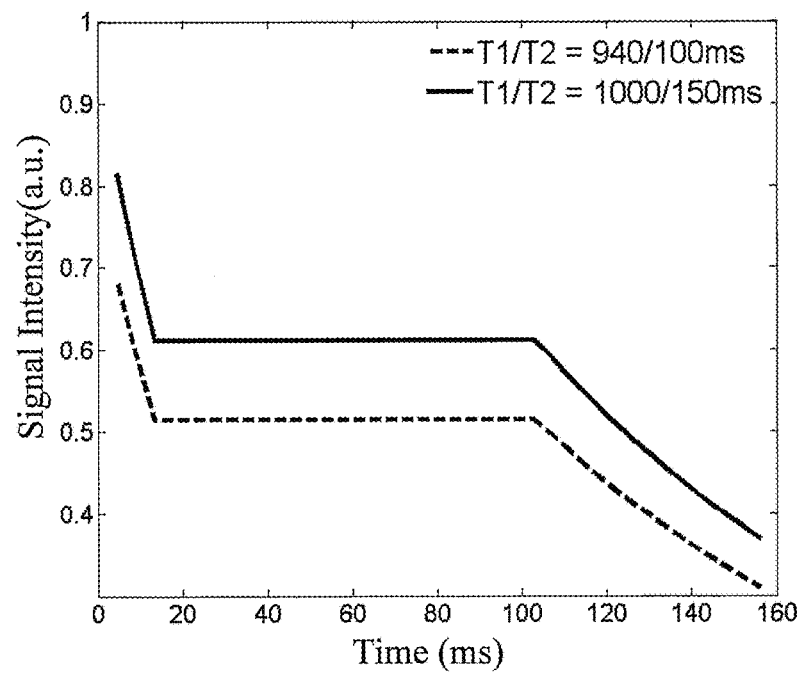
FIG. 13 illustrates a schematic diagram of a comparison between prescribed signal evolutions of the SPACE when T1/T2 is 940/100 ms and 1000/150 ms in an embodiment of the present invention, respectively.
Figure 14:
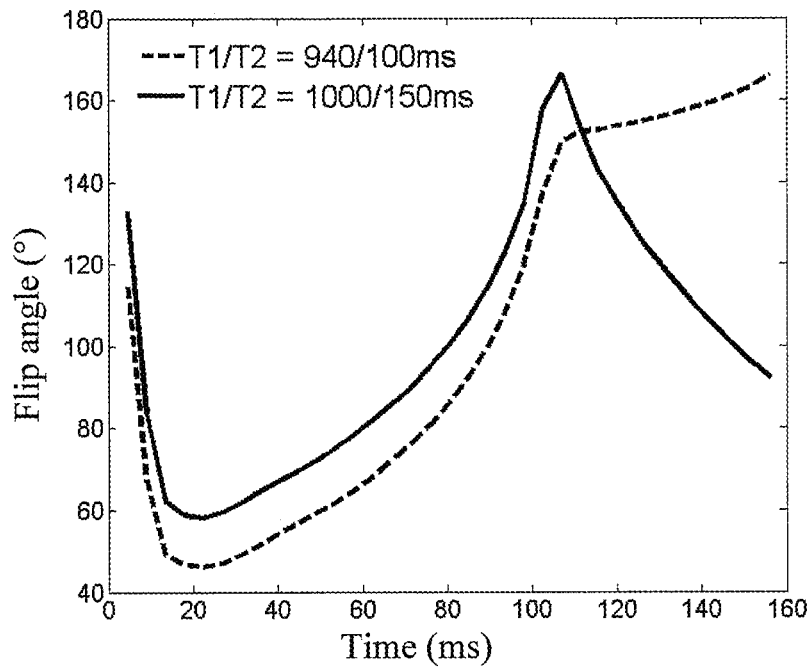
FIG. 14 illustrates a schematic diagram of a comparison between variable flip angles calculated from the prescribed signal evolutions as illustrated in FIG. 13.
Figure 15:
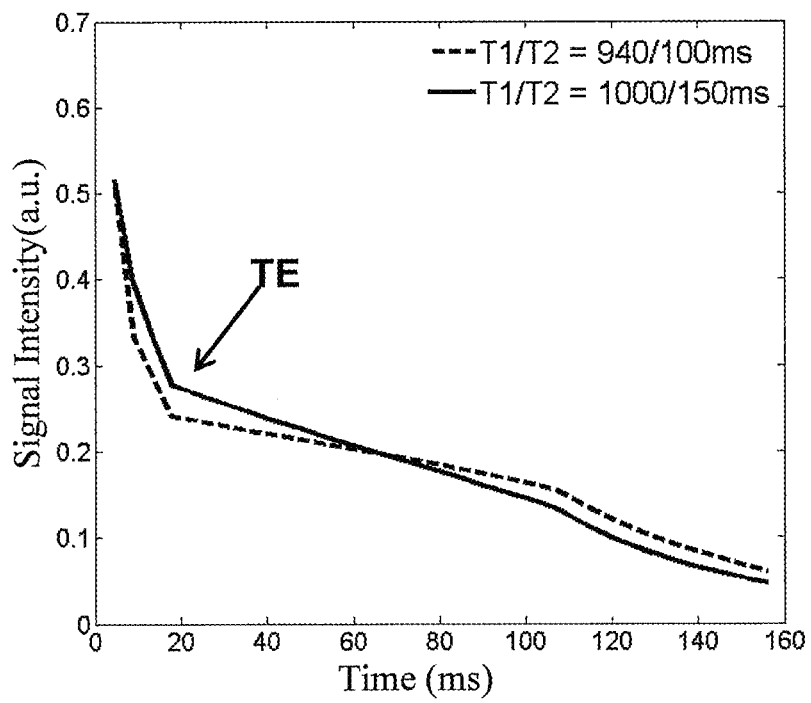
FIG. 15 illustrates a schematic diagram of a comparison between vessel wall signals calculated from the variable flip angles as illustrated in FIG. 14.

FIG. 13 illustrates a schematic diagram of a comparison between prescribed signal evolutions of SPACE when T1/T2 is 940/100 ms and 1000/150 ms in an embodiment of the present invention, respectively. As illustrated in FIG. 13, based on the 3T magnetic resonance imaging system, relative to the existed T1/T2 (commercial T1 and T2 are 940 ms and 100 ms, respectively), a stronger signal can be generated by setting the longitudinal magnetization vector relaxation time T1 and the transverse magnetization vector relaxation time T2 as 1000 ms and 150 ms, respectively. FIG. 14 illustrates a schematic diagram of a comparison between variable flip angles calculated from the prescribed signal evolutions as illustrated in FIG. 13. As illustrated in FIG. 14, relative to the existed T1/T2, larger variable flip angles can be obtained by setting the longitudinal magnetization vector relaxation time T1 and the transverse magnetization vector relaxation time T2 as 1000 ms and 150 ms, respectively. FIG. 15 illustrates a schematic diagram of a comparison between vessel wall signals calculated from the variable flip angles as illustrated in FIG. 14. As illustrated in FIG. 15, a vessel wall signal strength obtained from the optimized variable flip angle (T1/T2 is 1000/150 ms) is higher than a vessel wall signal strength obtained from the existed variable flip angles (T1/T2 is 940/100 ms), i.e., the vessel wall signal strength is increased by 15.6%. FIGS. 16A and 16B respectively illustrate a long axis magnetic resonance image and a short-axis magnetic resonance image of a vessel wall obtained using the variable flip angles when T1/T2 is 940/100 ms as illustrated in FIG. 14. The vessel wall short-axis magnetic resonance image as illustrated in FIG. 16B is a vessel wall short-axis image at the dotted line of FIG. 16A. FIGS. 17A and 17B respectively illustrate a long axis magnetic resonance image and a short-axis magnetic resonance image of a vessel wall obtained using the variable flip angles when T1/T2 is 1000/150 ms as illustrated in FIG. 14. The vessel wall short-axis magnetic resonance image as illustrated in FIG. 17B is a vessel wall short-axis image at the dotted line of FIG. 17A. As can be seen from the comparison between FIGS. 16A and 17A, and the comparison between FIGS. 16B and 17B, relative to the variable flip angles when T1/T2 is 940/100 ms, a stronger vessel wall signal can be obtained by applying the variable flip angles when T1/T2 is 1000/150 ms in the embodiment of the present invention into the vessel wall imaging, so as to more clearly distinguish the vessel wall in the imaging region.

By creatively designing a pulse sequence, and adding a flip-down pulse train behind the variable flip angle train of the three-dimensional fast spin echo (SPACE), the magnetic resonance vessel wall imaging method in the embodiment of the present invention effectively and uniformly further suppresses the cerebrospinal fluid signals of the whole brain, remedies the defect that the DANTE technique cannot uniformly suppress the cerebrospinal fluid signals, and further improves the magnetic resonance vessel wall imaging quality based on the technique combining the existed DANTE and SPACE. By adding a Delay Alternating with Nutation for Tailored Excitation (DANTE) pulse train in front of the variable flip angle train of the three-dimensional fast spin echo (SPACE), the advantages of DANTE can be remained to effectively suppress the blood flow signals, which promotes the vessel wall imaging of the head and neck jointing portion. Further, by optimizing SPACE, such as the variable flip angle train of SPACE, in various methods, the magnetic resonance imaging effect of the existed SPACE is better improved.

Based on the same invention conception of the magnetic resonance vessel wall imaging method as illustrated in FIG. 1, the embodiments of the present application further provide a magnetic resonance vessel wall imaging device, which will be described in the following embodiments. Since the magnetic resonance vessel wall imaging device solves its problem in a principle similar to that of the magnetic resonance vessel wall imaging method, the implementation of the magnetic resonance vessel wall imaging device may refer to that of the magnetic resonance vessel wall imaging method, and similar effects can be achieved, thus the repeated content is omitted. In the following description, the term "unit" or "module" can implement a combination of software and/or hardware of predetermined functions. Although the system described in the following embodiments is preferably implemented with software, hardware or the combination of software and hardware is also possible and conceivable.

FIG. 18 illustrates a structure diagram of a magnetic resonance vessel wall imaging device in an embodiment of the present invention. As illustrated in FIG. 18, a magnetic resonance vessel wall imaging device in an embodiment of the present invention may comprise a pulse sequence generation unit 210 and a magnetic resonance image generation unit 220 connected to each other.

The pulse sequence generation unit 210 is configured to apply a set pulse sequence into an imaging region, wherein the set pulse sequence comprises, in chronological order, a Delay Alternating with Nutation for Tailored Excitation (DANTE) pulse train, a variable flip angle train of a three-dimensional fast spin echo (SPACE), and a flip-down pulse train.

The magnetic resonance image generation unit 220 is configured to acquire a magnetic resonance signal generated in the imaging region, and reconstruct a magnetic resonance image of a vessel wall in the imaging region according to the magnetic resonance signal.

In some embodiments, the pulse sequence generation unit 210 may be further configured such that the flip-down pulse train comprises, in chronological order, a first pulse, a second pulse and a third pulse, wherein the time interval between the first pulse and the second pulse is one echo spacing, the time interval between the second pulse and the third pulse is a half of one echo spacing, and the flip angle of the third pulse is a 90°.

In some embodiments, the pulse sequence generation unit 210 may be further configured such that the flip angle of the first pulse is in the range of 100° to 150°, and the second pulse is in the range of 140° to 180°.

In some embodiments, the pulse sequence generation unit 210 may be further configured such that the flip angle of the first pulse is 130°, and the second pulse is 160°.

In some embodiments, the pulse sequence generation unit 210 may be further configured such that the DANTE pulse train comprises a plurality of pulse modules arranged in chronological order, each comprising one rectangular pulse and one dephasing gradient. The flip angle of the rectangular pulse may be in the range of 2° to 20°. The amplitude of the dephasing gradient may be set as a maximum operation value of the magnetic resonance system, such as 20 mT/m to 40 mT/m. The time duration of one pulse module may be about 1.5 ms, such as 1 ms to 2 ms. The number of repetitions of the pulse module may be adjusted depending on the application conditions, and for example may be set as 50 to 500.

Figure 19:
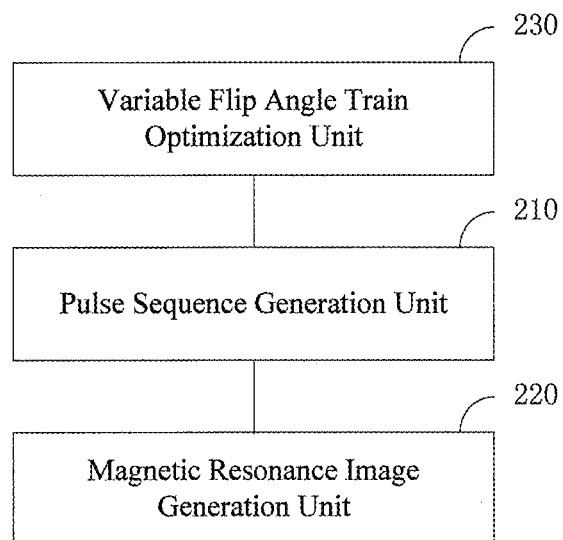
FIG. 19 illustrates a structure diagram of a magnetic resonance vessel wall imaging device in another embodiment of the present invention.

FIG. 19 illustrates a structure diagram of a magnetic resonance vessel wall imaging device in another embodiment of the present invention. As illustrated in FIG. 19, the magnetic resonance vessel wall imaging device as illustrated in FIG. 18 may further comprise a variable flip angle train optimization unit 230 connected to the pulse sequence generation unit 210.

The variable flip angle train optimization unit 230 is configured to optimize the variable flip angle train by adjusting longitudinal magnetization vector relaxation time T1 and/or transverse magnetization vector relaxation time T2, so as to improve a magnetic resonance image quality.

Figure 20:
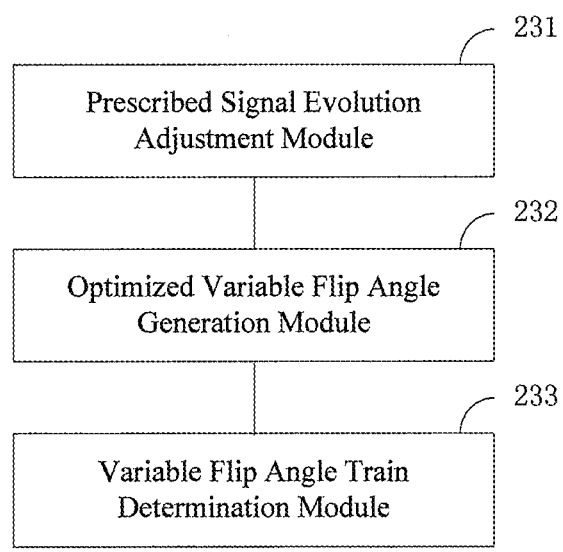
FIG. 20 illustrates a structure diagram of a variable flip angle train optimization unit in an embodiment of the present invention.

FIG. 20 illustrates a structure diagram of a variable flip angle train optimization unit in an embodiment of the present invention. As illustrated in FIG. 20, the variable flip angle train optimization unit 230 may comprise a prescribed signal evolution adjustment module 231, an optimized variable flip angle generation module 232 and a variable flip angle train determination module 233 which are connected in sequence.

The prescribed signal evolution adjustment module 231 is configured to adjust a prescribed signal evolution curve of SPACE by adjusting the longitudinal magnetization vector relaxation time T1 and/or the transverse magnetization vector relaxation time T2;

The optimized variable flip angle generation module 232 is configured to calculate an optimized variable flip angle from the prescribed signal evolution curve.

The variable flip angle train determination module 233 is configured to calculate actual signal evolution curves of a plurality of tissues according to the optimized variable flip angles, and judge whether to use the optimized variable flip angles as the variable flip angle train according to the actual signal evolution curves.

In some embodiments, the device is based on the 3T magnetic resonance system. The prescribed signal evolution adjustment module 231 may comprise a magnetization vector relaxation time setting module.

The magnetization vector relaxation time setting module is configured to set the prescribed signal evolution curve of SPACE by setting the longitudinal magnetization vector relaxation time T1 as 800 ms to 3000 ms, and/or setting the transverse magnetization vector relaxation time T2 as 150 ms to 200 ms.

In some embodiments, the magnetization vector relaxation time setting module 2311 comprises a magnetization vector relaxation time determination module configured to set the prescribed signal evolution curve of SPACE by setting the longitudinal magnetization vector relaxation time T1 as 1000 ms, and/or setting the transverse magnetization vector relaxation time T2 as 150 ms.

Figure 21:
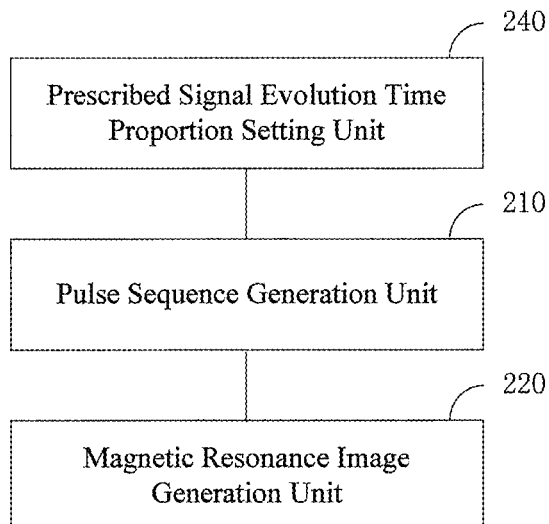
FIG. 21 illustrates a structure diagram of a magnetic resonance vessel wall imaging device in still another embodiment of the present invention.

FIG. 21 illustrates a structure diagram of a magnetic resonance vessel wall imaging device in still another embodiment of the present invention. As illustrated in FIG. 21, the magnetic resonance vessel wall imaging device as illustrated in FIG. 18 may further comprise a prescribed signal evolution time proportion setting unit 240 connected to the pulse sequence generation unit 210.

The prescribed signal evolution time proportion setting unit 240 is configured to optimize the variable flip angle train by adjusting time proportions of a first portion, a second portion and a third portion arranged in chronological order in a prescribed signal evolution curve of SPACE, so as to improve the magnetic resonance image quality.

Wherein, the length of the first portion is in the range of 2 to 5 echoes of the SPACE, and the duration of the second portion is in the range of 40% to 70% of total duration of the prescribed signal evolution curve.

Figure 22:
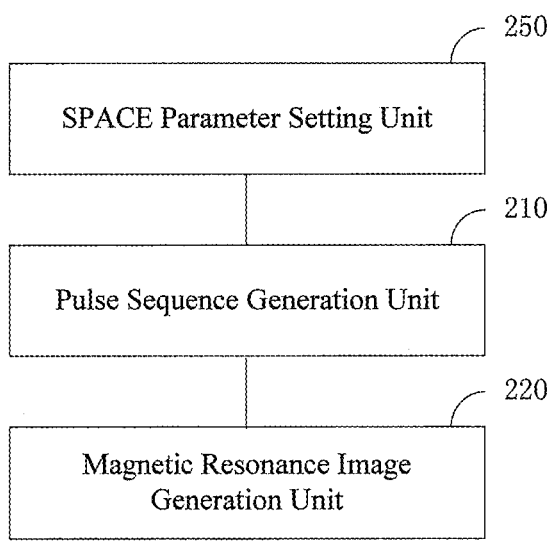
FIG. 22 illustrates a structure diagram of a magnetic resonance vessel wall imaging device in yet another embodiment of the present invention.

FIG. 22 illustrates a structure diagram of a magnetic resonance vessel wall imaging device in yet another embodiment of the present invention. As illustrated in FIG. 22, the magnetic resonance vessel wall imaging device as illustrated in FIG. 18 may further comprise SPACE parameter setting unit 250 connected to the pulse sequence generation unit 210.

SPACE parameter setting unit 250 is configured to optimize a magnetic resonance image by adjusting a plurality of parameters of SPACE.

Wherein the repetition time TR of SPACE is in the range of 800 ms to 1200 ms, the echo time TE of SPACE is in the range of 5 ms to 25 ms, and an echo train length of SPACE is in the range of 25 to 60.

By creatively setting a pulse sequence by the pulse generation unit, and adding a flip-down pulse train behind the variable flip angle train of the three-dimensional fast spin echo (SPACE), the magnetic resonance vessel wall imaging device in the embodiment of the present invention effectively and uniformly further suppresses the cerebrospinal fluid signals of the whole brain, remedies the defect that the DANTE technique cannot uniformly suppress the cerebrospinal fluid signals, and further improves the magnetic resonance vessel wall imaging quality based on the technique combining the existed DANTE and SPACE. By adding a Delay Alternating with Nutation for Tailored Excitation (DANTE) pulse train in front of the variable flip angle train of the three-dimensional fast spin echo (SPACE), the advantages of DANTE can be remained to effectively suppress the blood flow signals, which promotes the vessel wall imaging of the head and neck jointing portion. Further, by optimizing SPACE by various units or modules, e.g., optimizing the variable flip angle train of SPACE by the prescribed signal evolution time proportion setting unit and the variable flip angle train optimization unit, and optimizing the plurality of parameters of SPACE, the magnetic resonance imaging effect of the existed SPACE is better improved.

The embodiments of the present invention further provide a computer readable storage medium comprising computer readable instructions which enable, when being executed, a processor to at least perform one or more steps in the magnetic resonance vessel wall imaging method of the above embodiments.

Figure 23:
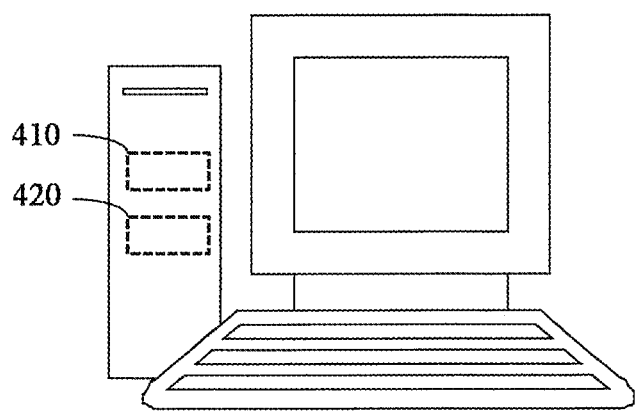
FIG. 23 illustrates a structure diagram of an equipment in an embodiment of the present invention.

The embodiments of the present invention further provide a device. FIG. 23 illustrates a structure diagram of the equipment in an embodiment of the present invention. As illustrated in FIG. 23, the equipment in an embodiment of the present invention may comprise a processor 410, and a memory 420 comprising computer readable instructions. The processor 410 at least performs one or more steps in the magnetic resonance vessel wall imaging method of the above embodiments when the computer readable instructions are executed.

In conclusion, by creatively designing a pulse sequence, and adding a flip-down pulse train behind the variable flip angle train of the three-dimensional fast spin echo (SPACE), the magnetic resonance vessel wall imaging method and device and the computer readable storage medium provided by the present invention effectively and uniformly further suppress the cerebrospinal fluid signals of the whole brain, remedy the defect that the DANTE technique cannot uniformly suppress the cerebrospinal fluid signals, and further improve the magnetic resonance vessel wall imaging quality based on the technique combining the existed DANTE and SPACE. By adding a Delay Alternating with Nutation for Tailored Excitation (DANTE) pulse train in front of the variable flip angle train of the three-dimensional fast spin echo (SPACE), the advantages of DANTE can be remained to effectively suppress the blood flow signals, which promotes the vessel wall imaging of the head and neck jointing portion. Further, by optimizing SPACE, such as the variable flip angle train of SPACE, through various methods, the magnetic resonance imaging effect of the existed SPACE is better improved.

In the descriptions of the Specification, the terms "an (one) embodiment", "an (one) specific embodiment", "some embodiments", "for example (such as)", "example", "specific example", "some examples", etc. mean that the specific features, structures, materials or characteristics described with reference to the embodiment(s) or example(s) are included in at least one embodiment or example of the present invention. In the Specification, the schematic description of any of those terms does not certainly mean the same embodiment or example. In addition, the described specific features, structures, materials or characteristics may be combined in a proper way in any one or more embodiments or examples. The sequence of the steps concerned in each embodiment just schematically describes the implementation of the present invention, wherein the sequence of the steps is not limited and may be appropriately adjusted upon demand.

A person skilled in the art shall appreciate that any embodiment of the present invention can be provided as a method, a system or a computer program product. Therefore, the present invention can take the form of a full hardware embodiment, a full software embodiment, or an embodiment combining software and hardware. Moreover, the present invention can take the form of a computer program product implemented on one or more computer usable storage mediums (including, but not limited to, a magnetic disc memory, CD-ROM, optical storage, etc.) containing therein computer usable program codes.

The present invention is described with reference to a flow diagram and/or block diagram of the method, device (system) and computer program product according to the embodiments of the present invention. It shall be understood that each flow and/or block in the flow diagram and/or block diagram and combinations thereof can be realized by the computer program instructions. These computer program instructions can be provided to a general computer, a dedicated computer, an embedded processor or a processor of other programmable data processing device to generate a machine, such that the instructions performed by the computer or the processor of other programmable data processing devices generate the device for implementing the function designated in one flow or a plurality of flows in the flow diagram and/or a block or a plurality of blocks in the block diagram.

These computer program instructions can also be stored in a computer readable memory capable of directing the computer or other programmable data processing devices to operate in a specific manner, such that the instructions stored in the computer readable memory generate a manufactured article including an instruction device that implements the function(s) designated in one flow or a plurality of flows in the flow diagram and/or a block or a plurality of blocks in the block diagram.

These computer program instructions can also be loaded onto a computer or other programmable data processing devices, such that a series of operation steps is executed on the computer or other programmable devices to generate the processing realized by the computer, therefore the instructions executed on the computer or other programmable devices provide the steps for implementing the function designated in one flow or a plurality of flows in the flow chart and/or a block or a plurality of blocks in the block diagram.

The above specific embodiments further describe the objectives, the technical solutions and the advantageous effects of the present invention in details. It shall be understood that those described are just specific embodiments of the present invention, rather than limitations to the protection scope of the present invention. Any amendment, equivalent replacement, improvement, etc. made within the spirit and principle of the present invention shall fall within the protection scope of the present invention.

What is claimed is:

1. A magnetic resonance vessel wall imaging method, comprising:
   applying a set pulse sequence into an imaging region, wherein the set pulse sequence comprises, in chronological order, a Delay Alternating with Nutation for Tailored Excitation (DANTE) pulse train, a variable flip angle train of a three-dimensional fast spin echo (SPACE), and a flip-down pulse train; and
   acquiring a magnetic resonance signal generated in the imaging region, and reconstructing magnetic resonance images of the vessel wall in the imaging region according to the magnetic resonance signal;
   wherein before applying a set pulse sequence into an imaging region, the method further comprises:
   optimizing the variable flip angle train by adjusting longitudinal magnetization vector relaxation time T1 and/or transverse magnetization vector relaxation time T2, so as to improve a magnetic resonance image quality.

2. The method according to claim 1, wherein optimizing the variable flip angle train by adjusting longitudinal magnetization vector relaxation time T1 and/or transverse magnetization vector relaxation time T2 comprises:
adjusting the prescribed signal evolution curve of SPACE by adjusting the longitudinal magnetization vector relaxation time T1 and/or the transverse magnetization vector relaxation time T2;
calculating the optimized variable flip angle series from the prescribed signal evolution curve; and
calculating actual signal evolution curves of a plurality of tissues according to the optimized variable flip angle series, and judging whether to use the optimized variable flip angles as the actual variable flip angle train according to the actual signal evolution curves.

3. The method according to claim 2, wherein the method is based on a 3T magnetic resonance system, and adjusting the prescribed signal evolution curve of SPACE by adjusting the longitudinal magnetization vector relaxation time T1 and/or the transverse magnetization vector relaxation time T2 comprises:
setting the prescribed signal evolution curve of SPACE by setting the longitudinal magnetization vector relaxation time T1 in the range of 800 ms to 3000 ms, and/or setting the transverse magnetization vector relaxation time T2 in the range of 150 ms to 200 ms.

4. The method according to claim 3, wherein setting the prescribed signal evolution curve of SPACE by setting the longitudinal magnetization vector relaxation time T1 as 800 ms to 3000 ms, and/or setting the transverse magnetization vector relaxation time T2 as 150 ms to 200 ms comprises:
setting the prescribed signal evolution curve of SPACE by setting the longitudinal magnetization vector relaxation time T1 as 1000 ms, and/or setting the transverse magnetization vector relaxation time T2 as 150 ms.

5. The method according to claim 1, wherein before applying a set pulse sequence into an imaging region, the method further comprises:
optimizing the variable flip angle train by adjusting time proportions of a first portion, a second portion and a third portion arranged in chronological order in the prescribed signal evolution curve of SPACE, so as to improve the magnetic resonance image quality;
wherein the length of the first portion is in the range of 2 to 5 echoes of the SPACE, and duration of the second portion is in the range of 40% to 70% of total duration of the prescribed signal evolution curve.

6. The method according to claim 1, wherein before applying a set pulse sequence into an imaging region, the method further comprises:
adjusting a plurality of parameters of SPACE so as to optimize a magnetic resonance image;
wherein the repetition time TR SPACE is in the range of 800 ms to 1200 ms, the echo time TE SPACE is in the range of 5 ms to 25 ms, and an echo train length SPACE is in the range of 25 to 60.

7. The method according to claim 1, wherein the flip-down pulse train comprises a first pulse, a second pulse and a third pulse in chronological order;
wherein the time interval between the first pulse and the second pulse is one echo spacing, the time interval between the second pulse and the third pulse is a half of one echo spacing, and the flip angle of the third pulse is 90°.

8. The method according to claim 7, wherein the flip angle of first pulse is in the range of 100° to 150°, and the second pulse is in the range of 140° to 180°.

9. The method according to claim 8, wherein the flip angle of the first pulse is 130°, and the second pulse is 160°.

10. The method according to claim 1, wherein the DANTE pulse train comprises a plurality of pulse modules arranged in chronological order, each comprising one rectangular pulse and one dephasing gradient; the flip angle of the rectangular pulse is in the range of 2° to 20°; the amplitude of the dephasing gradient is in the range of 20 mT/m to 40 mT/m; the time duration of one pulse module is in the range of 1 ms to 2 ms; and the number of repetitions of the pulse module is in the range of 50 to 500.

11. A computer readable storage medium comprising computer readable instructions, wherein the computer readable instructions enable, when being executed, a processor to at least perform the operations of:
applying a set pulse sequence into an imaging region, wherein the set pulse sequence comprises, in chronological order, a Delay Alternating with Nutation for Tailored Excitation (DANTE) pulse train, a variable flip angle train of a three-dimensional fast spin echo (SPACE), and a flip-down pulse train; and
acquiring a magnetic resonance signal generated in the imaging region, and reconstructing magnetic resonance images of the vessel wall in the imaging region according to the magnetic resonance signal;
wherein before applying a set pulse sequence into an imaging region, the method further comprises:
optimizing the variable flip angle train by adjusting longitudinal magnetization vector relaxation time T1 and/or transverse magnetization vector relaxation time T2, so as to improve a magnetic resonance image quality.

12. The computer readable storage medium according to claim 11, wherein when performing the step of optimizing the variable flip angle train by adjusting longitudinal magnetization vector relaxation time T1 and/or transverse magnetization vector relaxation time T2, the instructions further enable the processor to perform the operations of:
adjusting the prescribed signal evolution curve of SPACE by adjusting the longitudinal magnetization vector relaxation time T1 and/or the transverse magnetization vector relaxation time T2;
calculating the optimized variable flip angle series from the prescribed signal evolution curve; and
calculating actual signal evolution curves of a plurality of tissues according to the optimized variable flip angle series, and judging whether to use the optimized variable flip angles as the actual variable flip angle train according to the actual signal evolution curves.

13. The computer readable storage medium according to claim 12, wherein when performing the step of, based on a 3T magnetic resonance system, adjusting a prescribed signal evolution curve of SPACE by adjusting the longitudinal magnetization vector relaxation time T1 and/or the transverse magnetization vector relaxation time T2, the instructions further enable the processor to perform the operation of:
setting the prescribed signal evolution curve of SPACE by setting the longitudinal magnetization vector relaxation time T1 in the range of 800 ms to 3000 ms, and/or setting the transverse magnetization vector relaxation time T2 in the range of 150 ms to 200 ms.

14. The computer readable storage medium according to claim 13, wherein when performing the step of setting the prescribed signal evolution curve of SPACE by setting the longitudinal magnetization vector relaxation time T1 as 800 ms to 3000 ms, and/or setting the transverse magnetization vector relaxation time T2 as 150 ms to 200 ms, the instructions further enable the processor to perform the operation of:

setting the prescribed signal evolution curve of SPACE by setting the longitudinal magnetization vector relaxation time T1 as 1000 ms, and/or setting the transverse magnetization vector relaxation time T2 as 150 ms.

15. The computer readable storage medium according to claim 11, wherein before performing the step of applying a set pulse sequence into an imaging region, the instructions further enable the processor to perform the operations of:

optimizing the variable flip angle train by adjusting time proportions of a first portion, a second portion and a third portion arranged in chronological order in the prescribed signal evolution curve of SPACE, so as to improve the magnetic resonance image quality;

wherein the length of the first portion is in the range of 2 to 5 echoes of the SPACE, and duration of the second portion is adjusted as 40% to 70% of total duration of the prescribed signal evolution curve.

16. The computer readable storage medium according to claim 11, wherein before performing the step of applying a set pulse sequence into an imaging region, the instructions further enable the processor to perform the operations of:

adjusting a plurality of parameters of SPACE so as to optimize a magnetic resonance image;

wherein the repetition time TR of SPACE is in the range of 800 ms to 1200 ms, the echo time TE SPACE is in the range of 5 ms to 25 ms, and an echo train length SPACE is in the range of 25 to 60.

17. The computer readable storage medium according to claim 11, wherein the flip-down pulse train comprises a first pulse, a second pulse and a third pulse in chronological order;

wherein the time interval between the first pulse and the second pulse is one echo spacing, the time interval between the second pulse and the third pulse is a half of one echo spacing, and the flip angle of the third pulse is a 90°.

18. The computer readable storage medium according to claim 17, wherein the flip angle of the first pulse is in the range of 100° to 150°, and the second pulse is in the range of 140° to 180°.

19. The computer readable storage medium according to claim 18, wherein the first pulse is 130°, and the second pulse is 160°.

20. The computer readable storage medium according to claim 11, wherein the DANTE pulse train comprises a plurality of pulse modules arranged in chronological order, each comprising one rectangular pulse and one dephasing gradient; the flip angle of the rectangular pulse is in the range of 2° to 20°; the amplitude of the dephasing gradient is in the range of 20 mT/m to 40 mT/m; the time duration of one pulse module is in the range of 1 ms to 2 ms; and the number of repetitions of the pulse module is in the range of 50 to 500.

21. An equipment, comprising:
a memory comprising computer readable instructions; and
a processor configured to, when the computer readable instructions are executed, perform the operations of:
applying a set pulse sequence into an imaging region, wherein the set pulse sequence comprises, in chronological order, a Delay Alternating with Nutation for Tailored Excitation (DANTE) pulse train, a variable flip angle train of a three-dimensional fast spin echo (SPACE), and a flip-down pulse train; and acquiring a magnetic resonance signal generated in the imaging region, and reconstructing a magnetic resonance images of the vessel wall in the imaging region according to the magnetic resonance signal;

wherein before applying a set pulse sequence into an imaging region, the method further comprises:
optimizing the variable flip angle train by adjusting longitudinal magnetization vector relaxation time T1 and/or transverse magnetization vector relaxation time T2, so as to improve a magnetic resonance image quality.

22. The equipment according to claim 21, wherein when performing the step of optimizing the variable flip angle train by adjusting longitudinal magnetization vector relaxation time T1 and/or transverse magnetization vector relaxation time T2, the instructions further enable the processor to perform the operations of:

adjusting the prescribed signal evolution curve of SPACE by adjusting the longitudinal magnetization vector relaxation time T1 and/or the transverse magnetization vector relaxation time T2;

calculating the optimized variable flip angle series from the prescribed signal evolution curve; and calculating actual signal evolution curves of a plurality of tissues according to the optimized variable flip angle series, and judging whether to use the optimized variable flip angles as the actual variable flip angle train according to the actual signal evolution curves.

23. The equipment according to claim 22, wherein when performing the step of, based on a 3T magnetic resonance system, adjusting a prescribed signal evolution curve of SPACE by adjusting the longitudinal magnetization vector relaxation time T1 and/or the transverse magnetization vector relaxation time T2, the instructions further enable the processor to perform the operation of:

setting the prescribed signal evolution curve of SPACE by setting the longitudinal magnetization vector relaxation time T1 in the range of 800 ms to 3000 ms, and/or setting the transverse magnetization vector relaxation time T2 in the range of 150 ms to 200 ms.

24. The equipment according to claim 23, wherein when performing the step of setting the prescribed signal evolution curve of SPACE by setting the longitudinal magnetization vector relaxation time T1 as 800 ms to 3000 ms, and/or setting the transverse magnetization vector relaxation time T2 as 150 ms to 200 ms, the instructions further enable the processor to perform the operation of:

setting the prescribed signal evolution curve of SPACE by setting the longitudinal magnetization vector relaxation time T1 as 1000 ms, and/or setting the transverse magnetization vector relaxation time T2 as 150 ms.

25. The equipment according to claim 21, wherein before performing the step of applying a set pulse sequence into an imaging region, the instructions further enable the processor to perform the operation of:

optimizing the variable flip angle train by adjusting time proportions of a first portion, a second portion and a third portion arranged in chronological order in the prescribed signal evolution curve of SPACE, so as to improve the magnetic resonance image quality;

wherein the length of the first portion is in the range of 2 to 5 echoes of the SPACE, and the duration of the second portion is in the range of 40% to 70% of total duration of the prescribed signal evolution curve.

26. The equipment according to claim 21, wherein before performing the step of applying a set pulse sequence into an imaging region, the instructions further enable the processor to perform the operation of:

adjusting a plurality of parameters of SPACE so as to optimize a magnetic resonance image;

wherein the repetition time TR of SPACE is in the range of 800 ms to 1200 ms, the echo time TE of SPACE is in the range of 5 ms to 25 ms, and an echo train length of SPACE is in the range of 25 to 60.

27. The equipment according to claim 21, wherein the flip-down pulse train comprises a first pulse, a second pulse and a third pulse in chronological order;

wherein the time interval between the first pulse and the second pulse is one echo spacing, the time interval between the second pulse and the third pulse is a half of one echo spacing, and the flip angle of the third pulse is a 90°.

28. The equipment according to claim 27, wherein the flip angle of first pulse is in the range of 100° to 150°, and the second pulse is in the range of 140° to 180°.

29. The equipment according to claim 28, wherein the flip angle of first pulse is 130°, and the second pulse is 160°.

30. The equipment according to claim 21, wherein the DANTE pulse train comprises a plurality of pulse modules arranged in chronological order, each comprising one rectangular pulse and one dephasing gradient; the flip angle of the rectangular pulse is in the range of 2° to 20°; the amplitude of the dephasing gradient is in the range of 20 mT/m to 40 mT/m; the duration of one pulse module is in the range of 1 ms to 2 ms; and the number of repetitions of the pulse module is in the range of 50 to 500.

* * * * *